(12) United States Patent
Simon et al.

(10) Patent No.: US 8,082,038 B2
(45) Date of Patent: Dec. 20, 2011

(54) METHOD FOR TREATING DEGENERATIVE DISC DISEASE USING NONINVASIVE CAPACITIVELY COUPLED ELECTRICAL STIMULATION DEVICE

(75) Inventors: Bruce J. Simon, Mountain Lakes, NJ (US); Jean C. Gan, Morris Township, NJ (US)

(73) Assignee: EBI, LLC, Parsippany, NY (US)

( * ) Notice: Subject to any disclaimer, the term of this patent is extended or adjusted under 35 U.S.C. 154(b) by 405 days.

(21) Appl. No.: 11/176,588

(22) Filed: Jul. 7, 2005

(65) Prior Publication Data

US 2006/0030895 A1 Feb. 9, 2006

Related U.S. Application Data

(60) Provisional application No. 60/586,745, filed on Jul. 9, 2004.

(51) Int. Cl.
*A61N 1/32* (2006.01)
(52) U.S. Cl. ........................................................ 607/43
(58) Field of Classification Search .................... 607/43, 607/45
See application file for complete search history.

(56) References Cited

U.S. PATENT DOCUMENTS

| | | |
|---|---|---|
| 4,019,510 A | 4/1977 | Ellis |
| 4,461,300 A | 7/1984 | Christensen |
| 4,467,808 A | 8/1984 | Brighton et al. |
| 4,487,834 A | 12/1984 | Brighton |
| 4,535,775 A * | 8/1985 | Brighton et al. ................. 607/51 |
| 4,738,250 A | 4/1988 | Fulkerson |
| 4,846,181 A | 7/1989 | Miller |
| 4,895,154 A | 1/1990 | Bartelt et al. |
| 4,919,138 A | 4/1990 | Nordenstroöm |
| 4,982,742 A | 1/1991 | Claude |
| 4,993,413 A | 2/1991 | McLeod et al. |
| 5,014,699 A | 5/1991 | Pollack et al. |
| 5,038,780 A | 8/1991 | Boetzkes |
| 5,107,835 A | 4/1992 | Thomas |

(Continued)

FOREIGN PATENT DOCUMENTS

WO  WO 01/62336 A1  8/2001

(Continued)

OTHER PUBLICATIONS

Goodwin et al., "A Double-Blind Study of Capacitively Coupled Electrical Stimulation as an Adjunct to Lumbar Spinal Fusions," *SPINE*, vol. 24, No. 13, Jul. 1999, pp. 1349-1355.

(Continued)

*Primary Examiner* — George Evanisko
(74) *Attorney, Agent, or Firm* — William F. Bahret

(57) ABSTRACT

A method for treatment of degenerative disc disease using capacitively coupled electrical stimulation. In one embodiment, a subject diagnosed as having degenerative disc disease is treated by placing first and second electrodes on the subject's body at the site of an identified disc in a state of degenerative disc disease, and applying an electric field to the identified disc via the first and second electrodes with the intent to treat the degenerative disc disease. The electric field is created with an electrical signal having a frequency within a range of 20 to 100 kHz and having a symmetrical waveform with an amplitude within a range of 0.1 to 20 volts peak-to-peak, preferably a frequency of approximately 60 kHz and an amplitude of approximately 5 volts peak-to-peak.

5 Claims, 1 Drawing Sheet

U.S. PATENT DOCUMENTS

| | | | |
|---|---|---|---|
| 5,117,826 | A | 6/1992 | Bartelt et al. |
| 5,158,081 | A | 10/1992 | McWhorter et al. |
| 5,324,314 | A | 6/1994 | Boetzkes |
| 5,370,680 | A | 12/1994 | Proctor |
| 5,395,398 | A | 3/1995 | Rogozinski |
| 5,433,735 | A | 7/1995 | Zanakis et al. |
| 5,458,626 | A | 10/1995 | Krause |
| 5,607,461 | A | 3/1997 | Lathrop |
| 5,738,521 | A | 4/1998 | Dugot |
| 5,788,682 | A | 8/1998 | Maget |
| 5,814,094 | A | 9/1998 | Becker et al. |
| 5,861,016 | A | 1/1999 | Swing |
| 5,974,342 | A | 10/1999 | Petrofsky |
| 6,016,450 | A | 1/2000 | Crock |
| 6,048,301 | A | 4/2000 | Sabuda |
| 6,083,250 | A | 7/2000 | Lathrop |
| 6,132,357 | A | 10/2000 | Sabuda |
| 6,132,362 | A | 10/2000 | Tepper et al. |
| 6,334,069 | B1 | 12/2001 | George et al. |
| 2002/0128641 | A1 | 9/2002 | Underwood et al. |
| 2003/0130707 | A1 | 7/2003 | Gan et al. |
| 2004/0077921 | A1 | 4/2004 | Becker et al. |

FOREIGN PATENT DOCUMENTS

| | | | |
|---|---|---|---|
| WO | WO03/004092 | * | 1/2003 |

OTHER PUBLICATIONS

Brighton Carl T., et al., "Treatment of Castration-Induced Osteoporosis by a Capacitively Coupled Electrical Signal in Rat Vertebrae," *J. Bone and Joint Surg.*, 71-A: 228-236, 1989.

Brighton, Carl T., et al., "Treatment of Denervation/Disuse Osteoporosis in the Rat with a Capacitively Coupled Electrical Signal: Effects on Bone Formation and Bone Resorption," *J. Orthop. Res.*, 6:676-684, 1988.

J. Kantor et al., "Expected Healing Rates for Chronic Wounds," Medscape Pulmonary Medicine [online], vol. 12, No. 6, © 2000 [retrieved Mar. 26, 2001]. Retrieved from the Internet: http://www.medscape.com//HMP/wounds/2000/v12.n06/21206.02kant/pnt-w1206.02.kant.html.

L. C. Kloth et al., "Promotion of Wound Healing with Electrical Stimulation," *Advances in Wound Care*, vol. 9, No. 5, Sep./Oct. 1996, pp. 42-45.

D. J. Margolis et al., "Healing of Diabetic Neuropathic Foot Ulcers Receiving Standard Treatment A Meta-Analysis," *Diabetes Care*, vol. 22, No. 5, May 1999, pp. 692-695.

Martin C. Robson, M.D., "The Role of Growth Factors in the Healing of Chronic Wounds," *Wound Repair and Regeneration*, vol. 5, No. 1, Jan.-Mar. 1997, pp. 12-17.

K. Fukushima et al., "Studies on Galvanotaxis of Leukocytes," *Medical Journal of Osaka University*, vol. 4, No. 2-3, Nov. 1953, pp. 195-208.

C. A. Erickson et al., "Embryonic Fibroblast Motility and Orientation Can Be Influenced by Physiological Electric Fields," *The Journal of Cell Biology*, vol. 98, Jan. 1984, pp. 296-307.

N. Orida et al., "Directional Protrusive Pseudopodial Activity and Motility in Macrophages Induced by Extracellular Electric Fields," *Cell Motility*, vol. 2, 1982, pp. 243-255.

T. M. Mohr et al., "Effect of High Voltage Stimulation on Edema Reduction in the Rat Hind Limb," *Physical Therapy*, vol. 67, No. 11, Nov. 1987, pp. 1703-1707.

M. Brown, et al., "Polarity Effects on Wound Healing Using Electric Stimulation in Rabbits," *Arch. Phys. Med Rehabil.*, vol. 70, Aug. 1989, pp. 624-627.

M. Brown et al., "High-Voltage Galvanic Stimulation on Wound Healing in Guinea Pigs: Longer-Term Effects," *Arch. Phys. Med. Rehabil.*, vol. 76, Dec. 1995, pp. 1134-1137.

Brian V. Reed, "Effect of High Voltage Pulsed Electrical Stimulation on Microvascular Permeability to Plasma Proteins," *Physical Therapy*, vol. 68, No. 4, Apr. 1988, pp. 491-495.

V. Falanga et al., "Electrical Stimulation Increases the Expression of Fibroblast Receptors for Transforming Growth Factor-Beta," *J Invest Dermatol*, vol. 88, No. 4, Apr. 1987, Abstracts for the 1987 Annual Meeting of the Society for Investigative Dermatology, Inc., San Diego, California, May 4-6, 1987 (pp. 474 and 488).

C. B. Kincaid et al., "Inhibition of Bacterial Growth in Vitro Following Stimulation with High Voltage, Monophasic Pulsed Current," *Physical Therapy*, vol. 69, No. 8, Aug. 1989, pp. 651-655.

L. J. Laatsch et al., "In Vitro Effects of Two Silver Electrodes on Select Wound Pathogens," *Journal of Clinical Electrophysiology*, vol. 7, No. 1, pp. 10-15, 1995.

G. J. Bourguignon, "Electric Stimulation of Protein and DNA Synthesis in Human Fibroblasts," *FASEB Journal*, vol. 1, 1987, pp. 398-402.

N. I. Cruz et al., "Accelerated Healing of Full-Thickness Burns by the Use of High-Voltage Pulsed Galvanic Stimulation in the Pig," *Annals of Plastic Surgery*, vol. 23, Jul. 1989, pp. 49-55.

M. Brown et al., "Effects of High Voltage Stimulation on Cutaneous Wound Healing in Rabbits," *Physical Therapy*, vol. 67, No. 5, May 1987, pp. 662-667.

D. G. Lorich et al., "Biochemical Pathway Mediating the Response of Bone Cells to Capacitive Coupling," *Clinical Orthopaedics and Related Research*, No. 350, May 1998, pp. 246-256.

H. Zhuang et al., "Electrical Stimulation Induces the Level of TGF-$\beta 1$ mRNA in Osteoblastic Cells by a Mechanism Involving Calcium/Calmodulin Pathway," *Biochemical and Biophyscial Research Communications*, vol. 237, No. 2, 1997, pp. 225-229.

C. T. Brighton et al., "Present and Future of Electrically Induced Osteogenesis," in L.R. Straub and Wilson (ed.), *Clinical Trends in Orthopaedics*, Thieme Stratton publishers, 1981, pp. 10-12.

Biolectron SpinalPak® [online], undated [retrieved on Mar. 4, 2002]. Retrieved from the Internet: http://www.ebimedical.com/products/spine/spinalpak.html (2 pgs).

SpinalPak® Spine Fusion Stimulator [online], © 2001-2005 Retrieved from the Internet: http://www.ebimedical.com/surgeons/Osteobiologics/index.cfm?prodid=09020F (2 pgs).

SKANLAB 25 Bodywave Users Manual (13 pgs), c. Oct. 2003.

SKANLAB 25 Bodywave Technical specifications (3 pgs), c. Oct. 2003.

SKANLAB 25 Bodywave Examples of diagnosis and treatment information (3 pgs), c. Oct. 2003.

* cited by examiner

METHOD FOR TREATING DEGENERATIVE DISC DISEASE USING NONINVASIVE CAPACITIVELY COUPLED ELECTRICAL STIMULATION DEVICE

CROSS-REFERENCE TO RELATED APPLICATION

This application claims the benefit of Provisional Patent Application No. 60/586,745, filed Jul. 9, 2004, which application is hereby incorporated by reference.

BACKGROUND OF THE INVENTION

This invention relates to methods for treating degenerative disc disease, and more particularly to methods for treating degenerative disc disease noninvasively.

Degenerative disc disease (DDD), an irreversible process, is the most common cause of back pain. The intervertebral disc consists of a gelatinous nucleus pulposus encapsulated by a fibrous annulus fibrosus and the end-plates. The nucleus pulposus plays an important role in weight transmission. When this gel-like fluid is subjected to load, the nucleus pulposus is pressurized deforming to establish an equilibrating pressure between the annulus fibrosus and vertebral end-plates. However, with maturation, the tissue loses its gel-like properties becoming less hydrated and ultimately more fibrous. It is thus less able to transmit the load by exerting pressure on the annulus fibrosus. As a result, the annulus fibrosus undergoes greater deformation, and a greater share of the vertical load is borne directly by the annulus fibrosus. These changes result in the development of cracks and cavities within the annulus fibrosus leading to degeneration.

There are 3 therapeutic approaches to date:
1) Anti-neuralgic and anti-inflammatory;
2) Minimally invasive percutaneous treatments such as discectomy, intradiscal electrothermy, nucleoplasty and percutaneous radiofrequency application; and
3) Major surgeries such as fusions, laminectomy and nucleus/disc replacements.

Anti-neuralgic and anti-inflammatory methods treat the symptoms but do not eliminate the problem. Minimally invasive percutaneous treatments such as those identified above temporarily improve the symptoms, but they do not prevent the progression of DDD and may even accelerate it in the long term. Major surgeries such as those identified above eliminate structures, risk nerve injury during the operation, also risk morbidity, and may result in accelerated disc degeneration at adjacent segments in the long term.

SUMMARY OF THE INVENTION

The present invention provides for treatment of degenerative disc disease as a new indication for capacitively coupled electrical stimulation. According to one aspect of the present invention, a subject diagnosed as having degenerative disc disease is treated by placing first and second electrodes on the subject's body at the site of an identified disc in a state of degenerative disc disease, and applying an electric field to the identified disc via the first and second electrodes with the intent to treat the degenerative disc disease. The electric field is created with an electrical signal having a frequency within a range of 20 to 100 kHz and having a symmetrical waveform with an amplitude within a range of 0.1 to 20 volts peak-to-peak.

Treatment in accordance with the invention regenerates the intervertebral disc or prevents further degeneration of the disc and thus restores the mechanical properties of the spine or reduces pain resulting from disc degeneration (e.g., discogenic pain). The device may be used as an adjunct to other treatments such as implantation of cells (e.g., stem cells from various sources and intervertebral disc cells), biological factors (e.g., growth factors, peptides), scaffolds or materials (e.g., collagen, polymers, ceramics) and gene therapy.

Among other advantages of the present invention, it is a noninvasive and simple approach to relieving pain associated with the disc. It is simple to use, surgery is not required, the treatment can be administered early to prevent further progression of DDD, and it may regenerate the disc. Regeneration of the disc restores the mechanical properties of the spine, and thus, unlike other treatments such as spinal fusions, the present invention will not cause accelerated disc degeneration at adjacent segments in the long term.

These and other objects and advantages of the present invention will be more apparent upon reading the following detailed description in conjunction with the accompanying drawings.

DESCRIPTION OF PREFERRED EMBODIMENTS

Figure 1:
FIG. 1 is a rear view of the lower torso of a human subject with a pair of electrodes disposed on the skin proximate to the spine for treatment of degenerative disc disease according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

Figure 2:
FIG. 2 is a cross-sectional view of the portion of the spine proximate to the skin electrodes of FIG. 1.

The present invention provides a new method of treating degenerative disc disease (DDD) by using a noninvasive capacitively coupled electrical stimulation device that is compact, light and easy to use, and yet highly effective in operation. In the method according to one aspect of the present invention, two or more electrodes, e.g., electrodes 10 and 12 in FIGS. 1 and 2, are applied noninvasively on the skin at the site of pain or location of the intervertebral disc to be treated. For example, an electrode may be placed on either side of the spine at the level of a disc to be treated, with spacing of 4" to 6" between the electrodes. Suitable electrodes include those used with the SpinalPak spinal fusion stimulator, commercially available from EBI, L. P.

The electrodes are connected to a signal generator which emits a signal with a frequency of 20 to 100 kHz and having a symmetrical waveform with an amplitude of 0.1 to 20 volts peak-to-peak. Examples of signals are described in patent application Ser. No. 10/041,850, entitled Non-Invasive Capacitively Coupled Electrical Stimulation Device For Treatment Of Soft Tissue Wounds, filed Jan. 7, 2002 in the name of Jean C. Gan et al., which application is assigned to the assignee of the present invention and incorporated herein by reference. One preferred form of the signal is a symmetrical sine wave with a frequency of approximately 60 kHz and an amplitude of approximately 5 volts peak-to-peak. A bipolar DC signal with a symmetrical step or a triangular waveform may be useful in certain applications of the present invention. The signal is preferably applied intermittently but may be applied continuously for a period of time.

While the invention is not limited to any one theory of operation, it is believed that the invention promotes disc tissue regeneration and/or inhibits further progression of DDD by enhancing the proliferation and matrix synthesis of chondrocytes and stimulating the production of inflammatory cytokine antagonists, such as TGF-β. As indicated above, the invention may be used as an adjunct to other treatments such as implantation of cells, biological factors, scaffolds or materials, and gene therapy. The following additional patents and publications are hereby incorporated by reference along with all references cited therein: U.S. Pat. Nos. 4,467,808 and 4,535,775 to Brighton et al.; International Application No. PCT/U.S.01/05991 in the name of Brighton et al.; Brighton Carl T., et al., "Treatment of Castration-Induced Osteoporosis by a Capacitively Coupled Electrical Signal in Rat Vertebrae," J. Bone and Joint Surg., 71-A: 228-236, 1989; Brighton, Carl T., et al., "Treatment of Denervation/Disuse Osteoporosis in the Rat with a Capacitively Coupled Electrical Signal: Effects on Bone Formation and Bone Resorption," J. Orthop. Res., 6:676-684, 1988.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

We claim:

1. A nonsurgical method of treating degenerative disc disease, comprising:
   identifying a disc in a state of degenerative disc disease in a subject untreated by spinal fusion surgery; and
   nonsurgically treating the degenerative disc disease by applying capacitively coupled electrical stimulation to the identified disc untreated by spinal fusion surgery, intending to promote generation of disc tissue as an alternative to spinal fusion, the electrical stimulation characterized by an electric field created with an electrical signal having a frequency within a range of 20 to 100 kHz and having a symmetrical waveform with an amplitude within a range of 0.1 to 20 volts peak-to-peak.

2. The method of claim 1, wherein said electrical signal has a frequency of approximately 60 kHz and an amplitude of approximately 5 volts peak-to-peak.

3. The method of claim 2, wherein said electrical signal is a sine wave.

4. The method of claim 2, wherein said electrical signal is a bipolar DC signal with a square waveform.

5. The method of claim 2, wherein said electrical signal is a bipolar DC signal with a triangular waveform.

* * * * *